United States Patent [19]

Binger et al.

[11] Patent Number: 4,659,843

[45] Date of Patent: Apr. 21, 1987

[54] PROCESS FOR PREPARING 3-METHYL-2-BUTENE-4-OLIDE (4-METHYL-2(5H)-FURANE-2-ONE)

[75] Inventors: Paul Binger; Hans-Joachim Weintz, both of Mülheim/Ruhr, Fed. Rep. of Germany

[73] Assignee: Studiengesellschaft Kohle mbH, Mulheim/Ruhr, Fed. Rep. of Germany

[21] Appl. No.: 697,354

[22] Filed: Feb. 1, 1985

[30] Foreign Application Priority Data

Feb. 3, 1984 [DE] Fed. Rep. of Germany ....... 3403793

[51] Int. Cl.$^4$ ........................................... C07D 307/32
[52] U.S. Cl. ................................................... 549/295
[58] Field of Search ......................................... 549/295

[56] References Cited

FOREIGN PATENT DOCUMENTS 0015440 2/1980 Japan ................................. 549/295

OTHER PUBLICATIONS

Inoue et al., Journal Chem. Society Chem. Comm., 1979, pp. 982, Reacting of Methylenecyclopropanes with $CO_2$ Catalyzed by Pd(O) Complexes.
Sasaki et al, J.C.S. Chem. Comm., 1976, pp. 605–606, Rx of $CO_2$ with Butadiene Catalyzed by Pd Complexes.
Binger et al, Angew. Chem. Int. Ed. Engl., 16(1977), vol. 4, Pd(O) Catalyzed Cyclo Additions of Methylenecyclopropane to Alkenes.
Lee-Ruff; Can. J. Chem., vol. 50, No. 6, 3/72, pp. 952–955, Acid Catalyzed Rx of Cyclobutanones II.

Primary Examiner—Glennon H. Hollrah
Assistant Examiner—Dara Dinner
Attorney, Agent, or Firm—Sprung Horn Kramer & Woods

[57] ABSTRACT

The invention relates to a process for preparing 3-methyl-2-butene-4-olide by the codimerization of methylenecyclopropane with carbon dioxide ($CO_2$) in the presence of organic complex compounds of transistion metals, which process is characterized in that the codimerization is carried out at a temperature of 100° C. to 200° C. in the presence of palladium(O) compounds which are stable in the reaction mixture up to 200° C. and with $CO_2$ under a pressure of 10 to 110 bar, optionally in the presence of a solvent.

7 Claims, No Drawings

PROCESS FOR PREPARING 3-METHYL-2-BUTENE-4-OLIDE (4-METHYL-2(5H)-FURANE-2-ONE)

The present invention relates to a method for preparing 3-methyl-2-butene-4-olide(4-methyl-2(5H)-furane-2-one).

Catalyzed cycloadditions of methylenecyclopropanes with $CO_2$ palladium(O) compounds to form dihydrofurane-2-ones or methylene-tetrahydrofurane-2-ones, respectively, hitherto have only been described for methylenecyclopropanes that have been mono- or disubstituted at the double bond. Methylenecyclopropanes that have been substituted at the tri-membered ring do not undergo such a co-dimerization. (Literature: Y. Inoue, T. Hibi, M. Satake, H. Hashimoto, J. Chem. Soc. Chem. Comm. 1979, 982). Corresponding reactions by the basic member methylenecyclopropane (1) are unknown in the literature. According to a private oral communication by Y. Inoue they are reported to proceed very ununiform.

The reactions as known so far are represented by the following scheme:

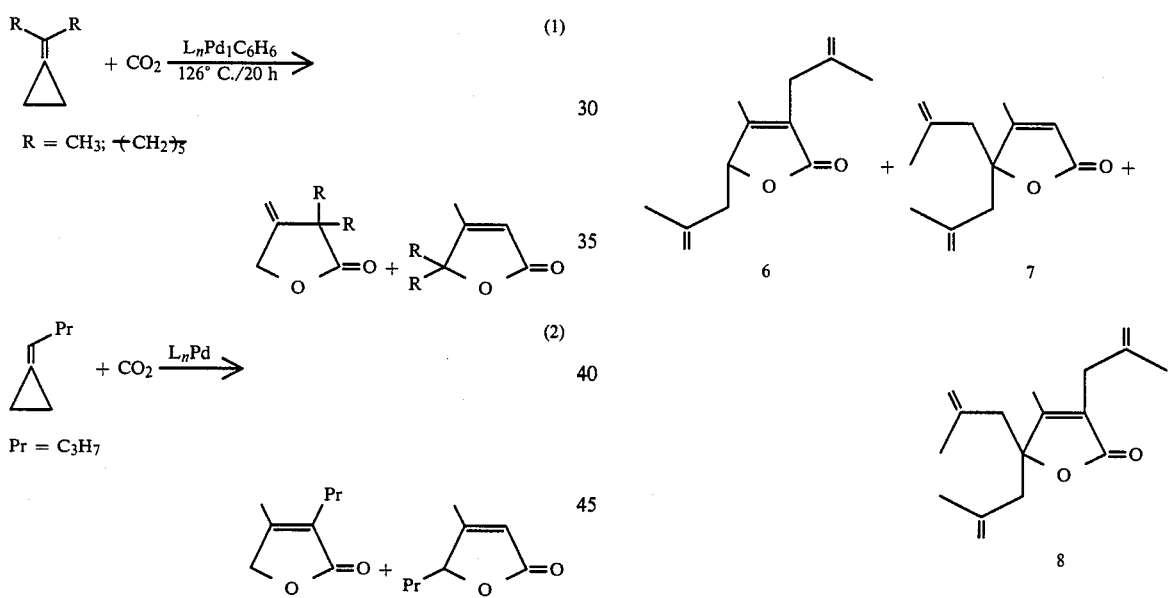

The abbreviations have the following meanings:
DMSO   dimethylsulfoxide;
DMF    dimethylformamide;
Pd(DBA)₂  bis(dibenzylideneacetone)palladium and
DBA    dibenzylideneacetone
$L_n$    triphenylphosphane, bis-(diphenylphosphoryl)-1,2-ethane It has now been found that the catalytic codimerization of methylenecyclopropane (1) with $CO_2$ on Pd(O) compounds can be smoothly carried out. For example, at 150° C. to 200° C. under a $CO_2$ pressure of 30 to 80 bar the 3-methyl-2-butane-4-olide (2) is obtained in a yield of up to 85%, up to 2000 moles of 1 being converted per mole of Pd atoms. In addition to the codimerization there also occurs a cyclodimerization of 1 to form 3 and an alkylation of 2 to form 4 through 8, 1 acting as the alkylating agent under the influence of the catalyst. Any other products are substantially not formed.

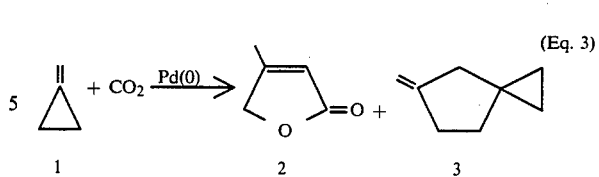

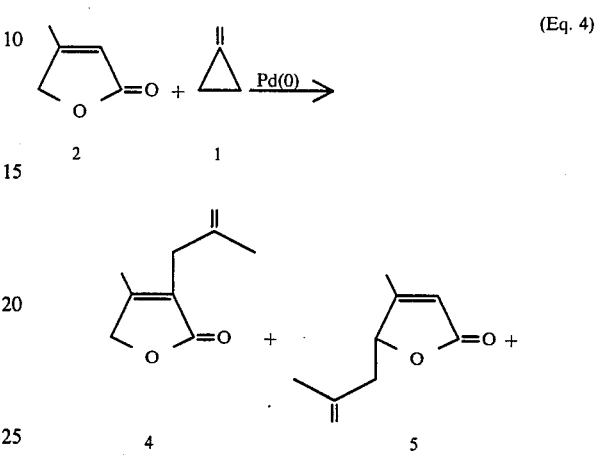

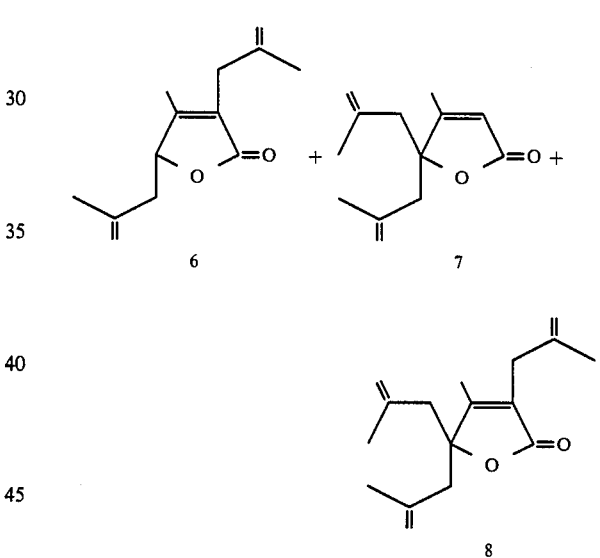

As the catalysts there are suitable all palladium(O) compounds that are stable in the reaction mixture up to 200° C. These include:

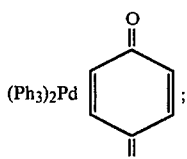

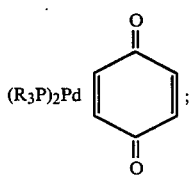

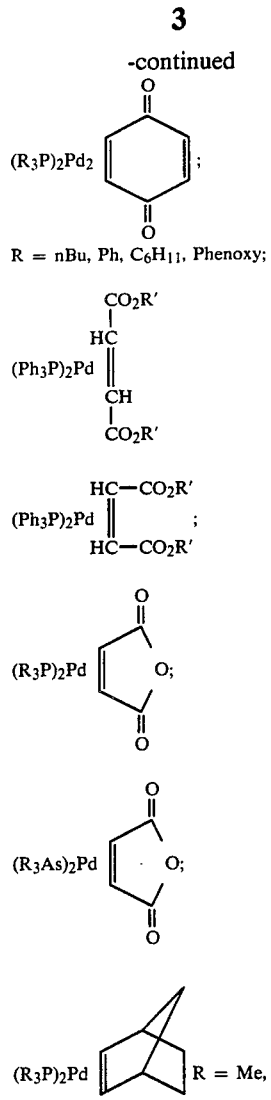

R = nBu, Ph, C$_6$H$_{11}$, Phenoxy;

(R$_2$P)$_2$Pd ... Ethylene, R = Me, C$_6$H$_{11}$;
(R$_2$P)$_2$PdCOD, R = Me, C$_6$H$_{11}$;
Pd(PPh$_3$)$_4$; Pd[PMe$_2$Ph]$_4$;
Pd[Me$_3$]$_4$; Pd[PMePh$_2$]$_4$; Pd[PEt$_3$]$_4$;
Pd[PBu$_3$]$_4$; Pd[P(iPr$_3$)]$_2$ and 3;
Pd[P(C$_6$H$_{11}$)$_3$]$_2$ and 3; Pd[P(tBu)$_2$Ph]$_2$;
Pd[P(CH$_2$Ph)$_3$]$_3$; Pd[PPh(tBu)$_2$]$_2$;
Pd[P(tBu)$_3$]$_2$;
(R$_3$P)$_2$Pd.AcN;
R = Alkyl, Phenyl, Alkoxy, Phenoxy;
(DBA)$_2$Pd; Pd$_2$(DBA)$_3$·S;
(Ph$_3$P)$_2$Pd$_2$(DBA)$_3$; [R$_3$P]$_3$Pd$_2$(DBA)$_3$;

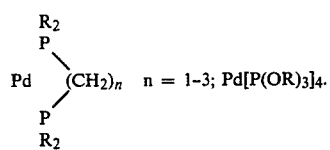

n = 1-3; Pd[P(OR)$_3$]$_4$.

Particularly reactive are mixtures in a ratio of from 1:2 to 1:8 of a Pd(O) compound such as, e.g. bis(dibenzylideneacetone)palladium [Pd(DBA)$_2$] (Lit.: T. Ukai, H. Kawazuma, Y. Ishi, J. J. Bennett and J. A. Ibers, J. Organomet. Chem. 65, 253 (1974)), bis(cyclooctadiene-1,5)palladium or tris(norbornene)palladium (Lit.: M. Green, J. A. K. Howard, J. L. Spencer and P. G. A. Stone, J. Chem. Soc. Chem. Comm. 1975, 449) with a trialkylphosphane, triarylphosphane, trialkylphosphite, triarylphosphite or a bidented bis(organylphosphoryl)-1,2-ethane or -1,3-propane.

Also Pd(O) catalysts prepared in situ are highly active. Such catalysts are prepared by reduction of Pd(II) compound such as, e.g., palladium acetylacetonate, palladium(II) nitrate, palladium(II) chloride, palladium(II) acetate with a metal organyl such as, e.g., lithiumbutyl, ethylmagnesium chloride or diethylethoxyaluminium in the presence of the aforementioned phosphanes or diphosphanes, respectively. Also a highly active magnesium or the combination of magnesium-/anthracene (Lit.: H. Bönnemann, B. Bogdanovic, German Pat. Specification No. 32 05 550.1; (Priority: Feb. 17, 1982); European Pat. No. 83 101 246.3 (Feb. 10, 1983), Studiengesellschaft Kohle mbH.) are well suitable as reducing agents. A particularly successful source of catalysts prepared in situ is the combination of $\eta^3$-allyl-$\eta^5$-cyclopentadienyl palladium (Lit.: Y. Tatsumo, T. Yoshida and S. Otsura, Inorg. Synth. 19, 220 (1979)) together with the aforementioned phosphanes or diphosphanes, respectively.

The preparation of the Pd(O) compounds and catalysts, respectively, has been described in P. Maitlis "The Organic Chemistry of Palladium", Vol. 1 (New York 1971) or in P. M. Maitlis and M. J. H. Russell, Comprehensive Organomet. Chem. Vol. 6, pp. 243–265, Pergamon Press 1982.

According to the invention the process is carried out at a temperature between 100° C. to 200° C., and preferably from 150° C. to 200° C., and under a pressure between 10 to 110 bar, and preferably from 30 to 80 bar. In said process a use of a solvent such, e.g., an aromatic (benzene, toluene, xylene), an ether (diethylether, tetrahydrofurane or dioxane) or of a different polar aprotic solvent (acetonitrile, dimethylsulfoxide, dimethylformamide) is beneficial. Nevertheless there may be operated without employing a solvent. A particularly high yield of 2 is obtained, while simultaneously the formation of 3 and of 4 through 8 is mostly suppressed, when the reactor is charged with CO$_2$ and part of the solvent (DMF) and the mixture comprising the catalyst and 1 is injected at a rate of from 1 to 20 ml/min per 200 ml of reaction volume at 150° C. to 200° C. The process according to the invention may be carried out batchwise (discontinuously), but alternative continuously as well.

The 3-methyl-2-butene-4-olide 2 is interesting as a starting compound for the synthesis of natural substances. Thus, it is possible, e.g., to synthesize the sidechain of α-tocopherol by starting from 2 (Lit.: M. Schmid, R. Barner, Helv. Chim. Acta 62, 464 (1979).

Also Rosefuran, the odor carrier of the Bulgarian rose oil is accessible from 2 (Lit.: D. R. Gedge and G. Pattenden, Tetrahedron Letters 1977, 4443).

The present invention is further illustrated by way of the following non-limiting examples which provide some working instructions:

EXAMPLE 1

An autoclave made of V4A steel having a capacity of 200 ml is charged with 15 ml of DMF and then heated to (an internal temperature of) 165° C. and pressurized with CO$_2$ to 40 bar. From a reservoir pressurized with nitrogen to 25 bar a solution of 0.5 g (0.28 mmol) of ($\eta^3$-allyl)-$\eta^5$-cyclopentadienyl)palladium, 0.27 g (1.1 mmol) of triphenylphosphane and 20.6 g (0.381 mol) of 1 in 90 ml of DMF is added by pumping using a metering pump during a period of about 1 hour. The pumping rate is chosen so that the temperature increase due to the exothermal reaction will not exceed 5° C.; the $CO_2$ pressure is kept constant at 40 bar. Upon completion of the addition stirring is continued for another hour. 145.7 g of a black reaction solution are discharged, from which all volatiles (142.7 g) up to a boiling point of 60° C./0.001 mbar are distilled off, leaving 1.9 g of a viscous black residue. A subsequent fractionating distillation using a 60 cm Vigreux column yields, after 109 g of DMF having a boiling point of about 50° C./7 mbar, 31 g of 2 (97% by GC; 80% of theory) having a boiling point of 131°–132° C./7 mbar; the remainder (GC) is 2.1% of 4 and 0.9% of 5. By means of a simple distillation there are obtained from the residue 6 g of a colorless liquid having a boiling range from 41° C. to 60° C./0.001 mbar having a composition (by GC) comprising 37.1% of 4; 46.4% of 5; 4.7% of 6; 6.7% of 7; 1.2% of 8; remainder (3.9%) 4 peaks.

EXAMPLE 2

In an analogous manner to that of Example 1 the autoclave is charged with 20 ml of DMF, heated to 150° C. and pressurized with $CO_2$ to 50 bar. Thereto is added by pumping a solution of 0.49 g (0.85 mmol) of Pd(DBA)$_2$, 0.89 g (3.4 mmol) of triphenylphosphane and 16 g (297 mmol) of 1 in 80 ml of DMF during 10 minutes, in the course of which addition the temperature is increased to a maximum of 190° C. and the pressure is increased to 65 bar for a short period of time. Upon an after-reaction taking thirty minutes the reaction has been completed. In the fractionating distillation there are obtained 25.8 g (85%) of 2.

EXAMPLE 3

In an analogous manner to that of Example 1 the autoclave is charged with 20 ml of DMSO, heated to 180° C. and pressurized with $CO_2$ to 30 bar. Thereto is added by pumping a solution of 0.45 g (about 0.5 mmol) of tetrakis(triphenylphosphane)palladium, 0.52 g (about 2 mmol) of triphenylphosphane and 16 g (297 mmol) of 1 in 180 ml of DMSO during 2 hours, while the $CO_2$ pressure is kept constant at 30 bar. As the result there are obtained 18.9 g (65%) of 2.

EXAMPLE 4

In an analogous manner to that of Example 1 there are obtained from 1 g (0.47 mmol) of $\eta^3$-allyl-$\eta^5$-cyclopentadienyl palladium, 0.97 g (3.76 mmol) of triphenylphosphane and 9.3 g (172 mmol) of 1 in 20 ml of DMF at 16 bar of $CO_2$ pressure (reaction temperature: 152° C.) 12.1 g of product showing the GC analysis as follows: 48% of 2; 21% of 4; 10% of 5; 11% of 6; 5% of 7 and 4% of 8.

EXAMPLE 5

In an analogous manner to that of Example 1 there are obtained from 0.49 g (0.85 mmol) of Pd(DBA)$_2$, 0.54 g (3.4 mmol) of triisopropylphosphane and 18.3 g (339 mmol) of 1 in 30 ml of DMF at 16 bar of $CO_2$ pressure (reaction temperature: 154° C.) 14.3 g of product showing the GC analysis as follows: 10.2% of 2; 15% of 3.; 7% of 4; 2% of 5; 40% of 6; 2% of 7 and 7% of 8; the remainder (27%) consists of a multitude of unidentified compounds each comprising between 0.5 and 2%.

EXAMPLE 6

Into an autoclave made of V4A steel and having a capacity of 200 ml there are filled, in sequence, 0.38 g (0.66 mmol) of Pd(DBA)$_2$, 0.72 g (2.64 mmol) of triphenylphosphane, 20 ml of toluene and, at −78° C., 12.8 g (237 mmol) of 1. The autoclave is pressurized with $CO_2$ to 40 bar at room temperature and is then heated at 130° C. (maximum pressure: 85 bar) while being shaken for 20 hours. The dark brown reaction solution is discharged and subjected to a fractionating distillation. After removal of 17.6 g of a colorless liquid having a boiling point up to 30° C. (12 mbar) showing a GC analysis of 97.7% of toluene and 2.3% of 3 (0.4 g (3.2% yield)) there are obtained 10.9 g of a liquid having a slightly yellow color and a boiling range of 35° C. to 70° C./0.001 mbar showing the GC analysis as follows: 23.6% of 2; 14.5% of 4; 8.2% of 5; 12.4% of 6; 2.5% of 7 and 6.8% of 8; the remainder of the volatiles (31.6%) consists of a multitude of unidentified compounds each comprising between 0.5 and 2%; distillation left 1.2 g of a viscous black residue.

EXAMPLE 7

In an analogous manner to that of Example 2 there are obtained from 0.13 g (0.61 mmol) of $\eta^3$-allyl-$\eta^5$-cyclopentadienyl palladium, 0.33 g (1.22 mmol) of triphenylylphosphane and 10 g (185 mmol) of 1 in 20 ml of DMF at 32 bar of $CO_2$ pressure after 15 hours at 144° C. 8 g of product showing the GC analysis as follows: 32% of 2; 22% of 4; 8% of 5; 6% of 6; 11% of 7 and 5% of 8; the remainder (16%) consists of a multitude of unidentified compounds each comprising between 0.5 and 2.4%.

EXAMPLE 8

In an analogous manner to that of Example 2 there are obtained from 0.14 g (0.66 mmol) of $\eta^3$-allyl-$\eta^5$-cyclopentadienyl palladium, 0.36 g (1.32 mmol) of triphenylylphosphane and 18 g (335 mmol) of 1 in 20 ml of DMSO at 32 bar of $CO_2$ pressure after 18 hours at 140° C. 10.5 g of product having a boiling range from 55° C. to 70° C./0.001 mbar and showing the GC analysis as follows: 3% of 4; 9% of 6; 4% of 7 and 69% of 8; the remainder (15%) consists of a multitude of unidentified compounds each comprising between 0.5 and 2%.

What is claimed is:

1. A process for preparing 3-methyl-2-butene-4-olide by the codimerization of methylene-cyclopropane with carbon dioxide ($CO_2$), characterized in that the codimerization is carried out at a temperature of 100° C. to 200° C. in the presence of a mixture of a palladium(O) compound and a phosphane or phosphite compound which mixture is stable in the reaction mixture, with $CO_2$ under a pressure of 10 to 110 bar.

2. The process according to claim 1, characterized in that the palladium(O) compounds are prepared in situ.

3. The process according to claim 1 characterized in that a temperature of 150° C. to 200° C. is employed.

4. The process according to claim 1 characterized in that a pressure of 30 to 80 bar is employed.

5. A process for preparing 3-methyl-2-butene-4-olide by the codimerization of methylene-cyclopropane with carbon dioxide ($CO_2$), characterized in that the codimerization employs a polar aprotic solvent and is carried out at a temperature of 100° C. to 200° C. in the presence of a mixture of a palladium(O) compound and a phosphane or phosphate compound which mixture is stable in the reaction mixture, with $CO_2$ under a pressure of 10 to 110 bar.

6. The process according to claim 5 characterized in that a solution of the palladium(O) compound having a concentration of 1 to 10-mmol/l of solvent is injected together with methylenecyclopropane (concentration of from 2 to 5 mol/l of solvent) into the solvent/$CO_2$ mixture (200 ml of reaction volume) at the reaction temperature and at a rate of 1 to 20 ml/minute without using any additional cooling.

7. The process according to claim 1, wherein the palladium(O) compound is a palladium(O)-phosphane compound.

* * * * *